(12) United States Patent
Hoeltke et al.

(10) Patent No.: US 7,645,369 B2
(45) Date of Patent: Jan. 12, 2010

(54) SEPARATION METHOD AND DEVICE FOR PROTEIN MIXTURES

(75) Inventors: Hans-Joachim Hoeltke, Penzberg (DE); Albert Roeder, Muensing (DE); Alois Rainer, München (DE); Peter Berndt, Basel (CH); Carlo Effenhauser, Weinheim (DE); Hanno Langen, Steinen (DE); Remo Anton Hochstrasser, Oberwil (CH)

(73) Assignee: Roche Diagnositcs Operations, Inc., Indianapolis, IN (US)

( * ) Notice: Subject to any disclaimer, the term of this patent is extended or adjusted under 35 U.S.C. 154(b) by 924 days.

(21) Appl. No.: 11/120,098

(22) Filed: May 2, 2005

(65) Prior Publication Data

US 2006/0000712 A1    Jan. 5, 2006

Related U.S. Application Data

(63) Continuation of application No. PCT/EP03/12320, filed on Nov. 5, 2003.

(30) Foreign Application Priority Data

Nov. 9, 2002    (DE) ................................ 102 52 177

(51) Int. Cl.
*G01N 27/447* (2006.01)
*G01N 27/453* (2006.01)

(52) U.S. Cl. ...................................... 204/451; 204/601
(58) Field of Classification Search ......... 204/450–470, 204/600–621
See application file for complete search history.

(56) References Cited

U.S. PATENT DOCUMENTS

| 3,704,217 | A | * | 11/1972 | Nerenberg | 210/635 |
| 4,181,594 | A | | 1/1980 | Rizk et al. | |
| 4,693,804 | A | * | 9/1987 | Serwer | 204/466 |
| 5,039,493 | A | | 8/1991 | Oprandy | |
| 5,279,721 | A | * | 1/1994 | Schmid | 204/457 |
| 5,580,434 | A | * | 12/1996 | Robotti et al. | 204/451 |
| 6,214,191 | B1 | | 4/2001 | Wiktorowicz et al. | |

FOREIGN PATENT DOCUMENTS

| DE | 4114611 AL | 11/1991 |
| DE | 4408034 C1 | 7/1995 |
| EP | 0300924 B1 | 3/1993 |
| WO | WO 87/02132 | 4/1987 |

OTHER PUBLICATIONS

Becker, H. et al., "Planar quartz chips with submicron channels for two-dimensional capillary electrophoresis applications," J. Micromech. Mircoeng. 8 (1998) 24-28.

* cited by examiner

*Primary Examiner*—Alex Noguerola
(74) *Attorney, Agent, or Firm*—Marilyn Amick; Roche Diagnostics Operations, Inc.

(57) ABSTRACT

A separation device and a separation method for biomolecular sample material and in particular protein mixtures. For this purpose a separation element 10 for the two-dimensional and preferable electrophoretic separation of components of the sample material is provided in area 30 of a separation plane. According to the invention it is proposed that the separation element 10 has a channel or transfer structure 14 for the locally resolved discharge of separated sample components in a transport direction that is at right angles to the separation plane onto a support surface 16 that is preferably suitable for mass spectroscopic analyses.

22 Claims, 6 Drawing Sheets

SEPARATION METHOD AND DEVICE FOR PROTEIN MIXTURES

RELATED APPLICATIONS

This application is a continuation of international application PCT/EP03/12320 filed Nov. 5, 2003, which claims priority to German application DE 10252177.8 filed Nov. 9, 2002.

FIELD OF THE INVENTION

The invention concerns a separation device and a separation method for biomolecular sample material and in particular for protein mixtures.

BACKGROUND

Deciphering the human genome, i.e., the sequencing of the entire genetic information of humans, was a milestone in molecular biological research. Research is now focused on deciphering the function of the genome and on the gene products, the proteins. Here one would like to have the most complete possible picture of all proteins expressed in a certain cell population or in a certain tissue. The identity and quantity of the proteins should be correlated to a certain development stage or to the physiological state of the cell or tissue. Thus one would like to obtain a picture of all proteins that is as accurate and quantitative as possible in order to come closer to a functional description. This research of the "post genome" era is also referred to as proteomics. Whereas the genome is basically a static entity, the proteome of a living organism is characterized by its ability to change depending on the temperature, nutrient milieu, and the action of stress or drugs. It therefore comprises the totality of the proteins that are synthesized by the genes of a cell or an organism under certain environmental conditions in various growth phases.

Proteomics is intended to yield new information on the function, regulation, and interaction of proteins by identifying and quantifying all proteins. In particular the aim is to reveal quantifiable differences between normal cells and "degenerate" cancer cells or differences in the protein repertoire of "diseased" and "healthy". This in turn allows a specific search for therapeutically active substances.

In order to analyze a proteome, the total amount of proteins is separated into its individual components, i.e., the many thousands of individual proteins are physically separated from the mixture. This is usually achieved by so-called two-dimensional (2-D) electrophoresis. In this process, the total proteins from a cell population or tissue are isolated as quantitatively as possible. If necessary certain fractionation steps are also carried out if one wants to specifically examine only a certain fraction of the total proteins, e.g., proteins from certain cell organelles such as the mitochondria.

Then an isoelectric focusing (IEF) is carried out in the first dimension which separates the proteins in a special gel or on a solid support in a pH gradient on the basis of their isoelectric point (pI). The proteins migrate in the electrical field and are focused at their pI which is characteristic for each protein. This first step of isoelectric focusing requires certain electrophoresis equipment to hold membranes or strips with immobilized pH gradients or gels with ampholyte buffers. The isoelectric focusing process usually takes many hours (24 to 48 h).

After the isoelectric focusing is completed, the gels or membranes are usually removed from the first apparatus and equilibrated in an electrophoresis buffer containing SDS (sodium dodecyl sulfate). Then each gel or each membrane is placed on a new second gel in a second gel apparatus. These second gels consist of SDS/polyacrylamide. After applying an electrical potential perpendicular to the IEF gel, the focused proteins migrate into the second gel and are separated there according to their molecular weight. This electrophoretic separation can also take many hours (>16 h).

In the next step the proteins separated in this manner are visualized. This occurs by a staining step using Coomassie Brilliant Blue, colloidal Coomassie, silver nitrate, or fluorescent dyes (SYPRO Red, SYPRO Ruby). Subsequently the stained gel is photographed, usually with a digital imaging system, or the stained spots are documented. In order to be able to make a more accurate scientific statement, either all stained proteins or certain proteins of interest (e.g. those whose position and/or quantity has changed relative to a reference) are identified and characterized. This is normally carried out by mass spectroscopic methods. The most commonly used method is the analysis of peptide fragments of a certain spot by MALDI-TOF (matrix-assisted laser desorption/ionization time-of-flight) mass spectrometry. For this, a multistep processing of the individual stained protein spots is again carried out.

In the first step the stained protein spots are isolated from the gel in the smallest possible volume. This is carried out manually or with automatic software-controlled spot pickers. The small protein-containing pieces of gel (a few µl volume) are then incubated with a buffer which ensures that SDS and the dye are removed from the gel. Then the gel pieces are dried, taken up in a buffer suitable for protease digestion and incubated with a protease (usually trypsin). This cleaves the proteins in the gel into defined fragments. Subsequently the protein fragments (peptides) are washed out of the gel or eluted with ammonium bicarbonate.

The peptides isolated from the individual gel pieces are then applied separately to a support for mass spectrometry and subjected to mass spectrometry (MALDI-TOF) after drying and optionally recrystallization. The data from the mass spectrometry allow an unequivocal identification of the protein and a relative quantification of the amount of protein by comparison with suitable databases.

The classical 2-D electrophoresis method described above with processing for mass spectrometry has a number of disadvantages:

It requires relatively large amounts of total protein (milligram). These amounts are often not available especially for problems of particular interest e.g. when examining tumour tissue.

It is very time consuming and laborious.

It includes very many steps that in some cases can only be carried out manually.

It requires a large amount of equipment (IEF electrophoresis, SDS-PAGE electrophoresis, stainer, imager, spot-picker, gel piece incubator, dryer, automatic pipettor, etc.)

It only allows separation of proteins that are suitable for IEF. Many classes of protein and especially those that are of particular interest, e.g., membrane proteins/receptors, cell nuclei- or DNA-associated proteins, cannot be separated by IEF or not adequately.

The overall process is not very reproducible.

Although electrophoresis chips have been described in the literature or in patent applications (U.S. Pat. No. 6,214,191, U.S. Pat. No. 5,599,432, EP 977030, WO 0058721; Becker et al., J. Micromech. Microeng. 1988, 8, 24) for two-dimensional separation of proteins, they are not yet available as a product or as prototypes and cannot be tested. Methods for optical detection were described for the further processing, but no data that were obtained by the method were shown. Although such chips have the advantage of being able to separate very small amounts of protein, it is, however, clear to a person skilled in the art that these very small amounts can hardly still be optically detected.

SUMMARY OF THE INVENTION

In summary, the invention concerns a separation device and a separation method for biomolecular sample material and in particular protein mixtures. For this purpose, a separation element 10 for the two-dimensional and preferable electrophoretic separation of components of the sample material is provided in area 30 of a separation plane. According to the invention it is proposed that the separation element 10 has a channel or transfer structure 14 for the locally resolved discharge of separated sample components in a transport direction that is at right angles to the separation plane onto a support surface 16 that is preferably suitable for mass spectroscopic analyses.

BRIEF DESCRIPTION OF THE DRAWINGS

The following is shown schematically.

DETAILED DESCRIPTION

Figure 1:
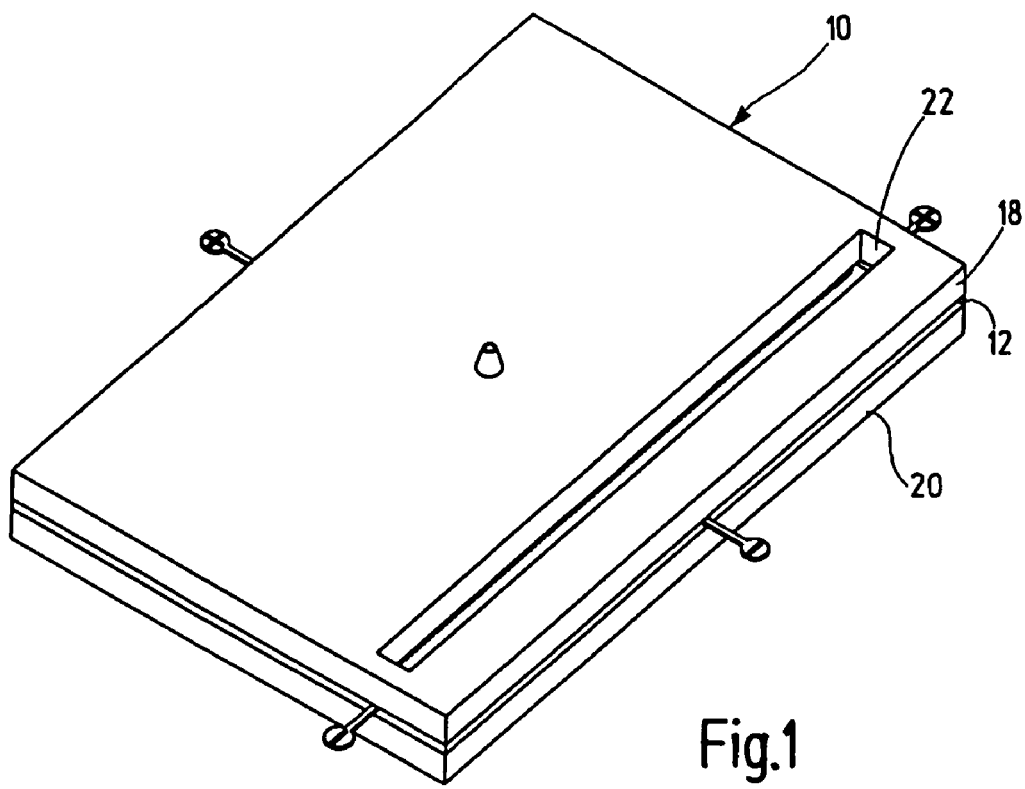
FIGS. 1 and 2 show a device for separating and processing proteins comprising a plate-shaped separation element in a perspective and vertically truncated representation.

On this basis, the object of the invention is to avoid the disadvantages of the prior art and to improve a device and method of the type stated above such that it is also possible to reliably and very accurately process or analyze very small amounts of protein in a process that can be automated and is easy to handle.

The combination of features stated in the independent patent claims is proposed to achieve this object.

The invention is based on the idea of creating a three-dimensional transport structure for the sample material that is integrated into a structural component in order to enable sample components to be specifically processed in addition to being separated. Accordingly the invention proposes that the separation element has a channel structure to discharge separated sample components onto a support surface in a transport direction at right angles to the separation plane. Consequently from a process point of view, the invention provides that the separated sample components are discharged onto a support surface from the separation element at right angles to the separation plane.

The invention allows a rapid separation of proteins that can be readily automated and a direct, spatially resolved discharge onto a support surface or substrate in a single three-dimensional basic element. Hence it is possible to transfer the information content contained in a two-dimensional protein separation into the third dimension without information loss. According to the invention, the entire process chain which would otherwise be carried out in separate devices, is combined in a single element. In particular, the manual steps are reduced to the application of the sample. The amount of biological material required can be reduced by several orders of magnitude such that microgram amounts are sufficient for an analysis. By integrating partial steps into a single structural element and by omission of manual intermediate steps, the overall process becomes considerably more reproducible and controllable. In addition, the duration of the entire process can be reduced to a few hours. This allows entirely new types of objects to be processed which were previously not amenable due to the relatively large amount of material required and enables a very much finer discrimination of biological processes. The substances (e.g. peptides) deposited on a free surface of the separation element can be analysed directly, for example, by mass spectroscopy. Optionally a special target plate for mass spectroscopy is provided as the support substrate. Other applications are basically conceivable, for example, functional assays for activity or binding tests of the separated proteins or peptides.

Advantageous embodiments and further developments of the invention result from the dependent claims and from the following description of examples of application and the drawings.

The plate-shaped separation elements 10 shown in the drawings comprise a separation plate 12 for the two-dimensional separation of protein material, a transport or channel structure 14 that is active at right angles thereto for discharging the separated sample components true to position onto a support surface 16 that is suitable for mass spectroscopic analyses and a cover plate 18 and a bottom plate 20 to border both sides of the separation plate 12.

Figure 2:
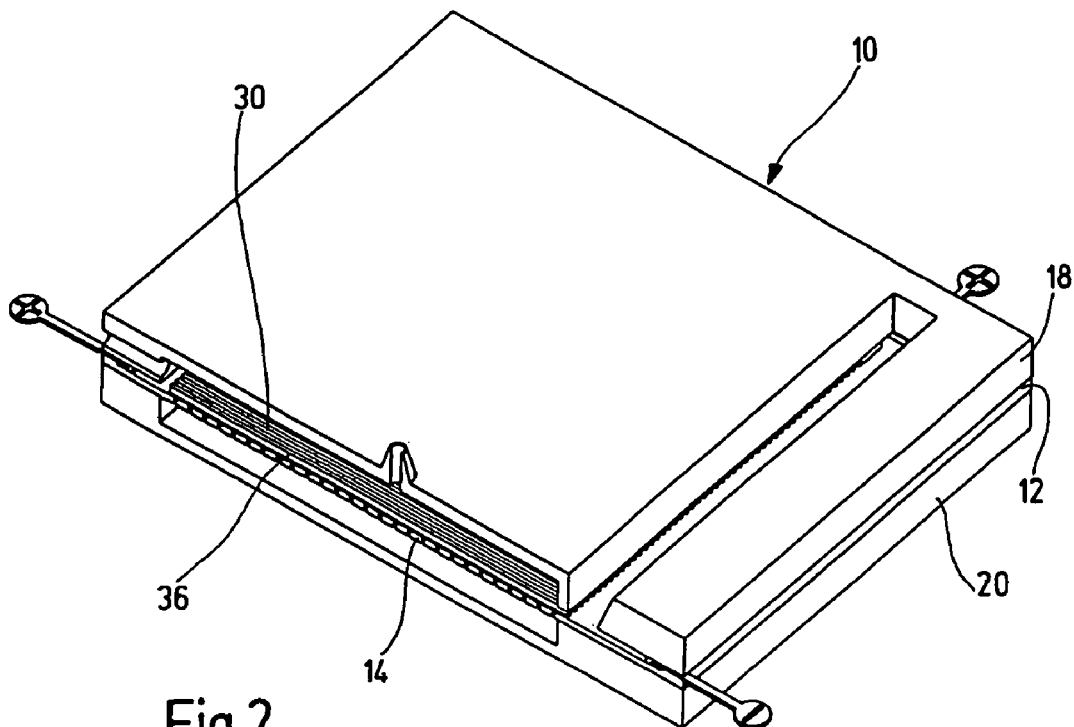
Figure 3:
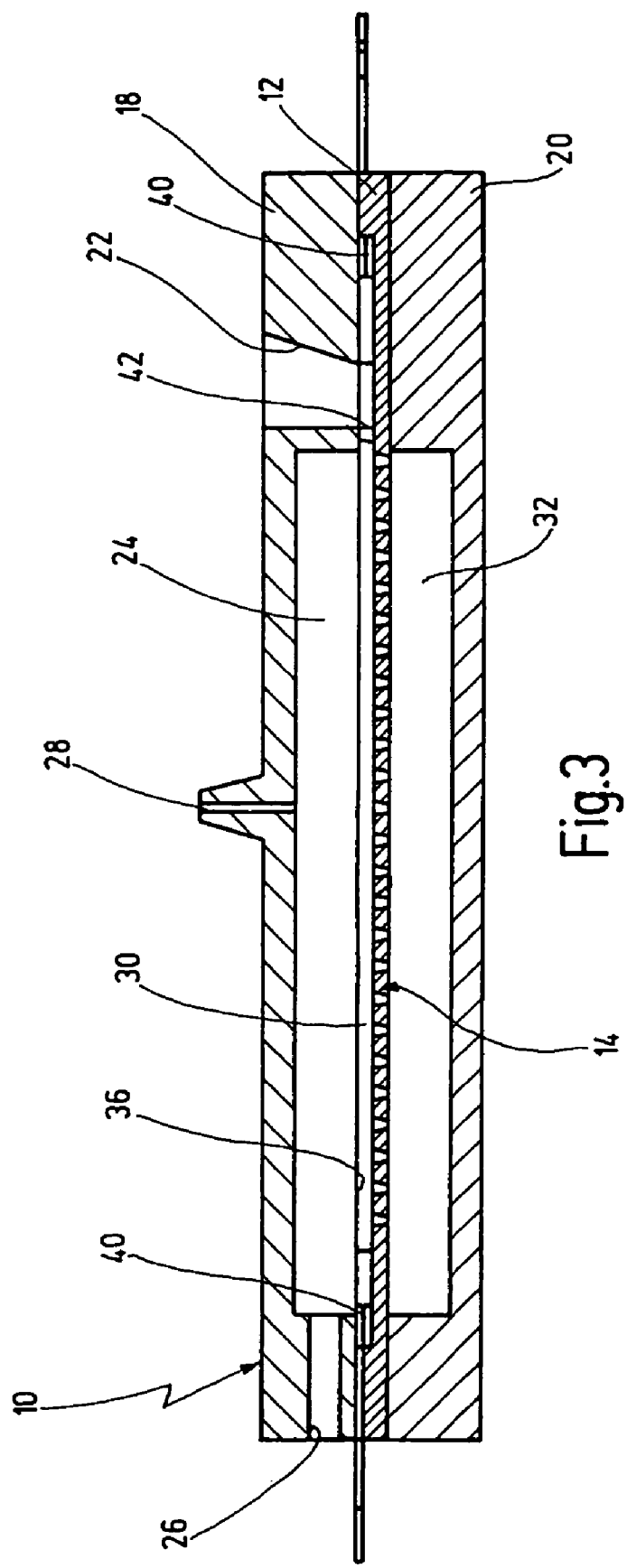
FIG. 3 shows a vertical section through the separation element according to FIG. 1.

As shown in FIGS. 1 to 3, the cover plate 18 has a slit-shaped opening therethrough 22 for sample application, a cover chamber 24 which is open towards the separation plate 12, a lateral inlet opening 26 which opens into the cover chamber 24 and a central valve opening 28. The separation plate 12 forms a three-dimensional channel system in two overlying areas, one of which is bounded on its bottom side in the upper two-dimensional separation area 30 lying in the plate or separation plane by the channel structure 14 running in the third dimension. The bottom plate 20 serves to support and stabilize the plate arrangement and contains a collecting chamber 32 which is open towards the channel structure 14.

The base material for the separation element 10 designed as a composite chip can consist of silicon, polypropylene, polycarbonate, other polymers (e.g. polymethyl-methacrylate, polyethylene terephthalate, polystyrene, polydimethylsiloxane), artificial resin, ceramic or a metal or a variety of these materials. It is important that the base material allows moulding with the necessary precision and is compatible with the materials used for sample processing. The base material should expediently be electrically insulating and thermally conductive to enable electrophoretic separations and optionally an efficient cooling. The separation element 10 has, for example, a basal area of 6÷4 cm (corresponding to ¼ of a conventional microtitre plate).

Figure 4:
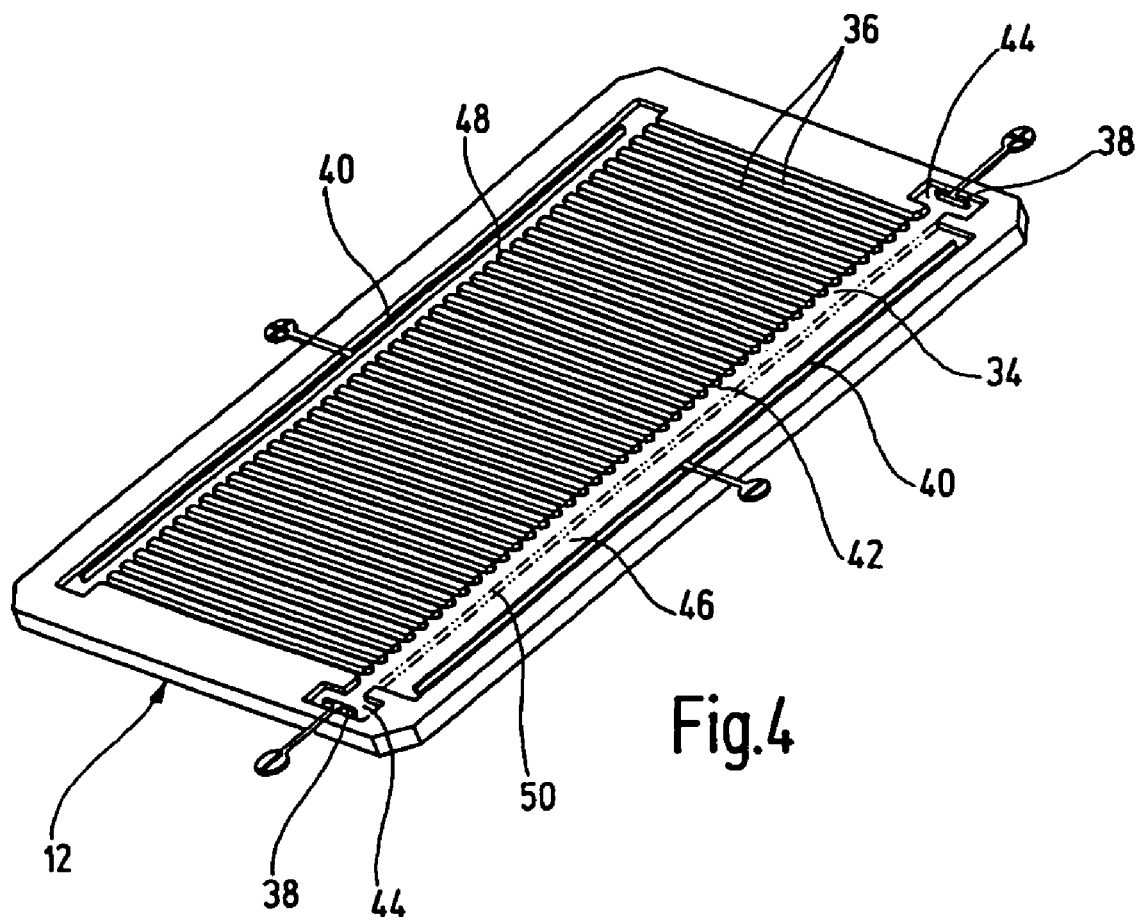
FIG. 4 shows middle or separation plate of the separation element in a perspective view.

The separation plate 12 which is shown separately in FIG. 4 has orthogonal separation paths 34, 36 in the plate plane for sequential 2D electrophoresis. Two electrode pairs 38, 40 are provided for this purpose to which a suitable direct current voltage can be applied via electrical connecting lugs.

The separation path 34 of the first dimension between the electrodes 38 is formed by an elongate recess 42 in which a gel or membrane strip (not shown) with a preformed pH gradient is placed in order to isoelectrically focus (IEF) the protein molecules. For this purpose an electrophoresis buffer can be previously placed in storage zones 44 in the area of the electrodes 38.

The separation paths of the second dimension are formed by a group of parallel channels 36 extending between the electrodes 40 which are distributed along the recess 42 and branch at right angles thereto. The number of channels depends on the desired and achievable resolution or separation efficiency of the first dimension. It can be between 10 and several thousand, preferably 50 to 500. Molecules are separated in these channels by polyacrylamide gel electrophoresis (PAGE) in a electrophoresis buffer containing sodium dodecyl sulfate (SDS). In this connection, the recesses 46, 48 in the area of the electrodes 40 can serve as a buffer reservoir.

In the manufacturing process, the SDS-PAGE separation gel is first introduced into the channels 36 of the second dimension and into the buffer reservoirs 46, 48 and photopolymerized. In this connection, the recess 42 for the IEF gel strips can be mechanically separated (separator 50) to prevent an intermixing of the gel types. It is also advantageous when the initial part of the channels 36 is filled with a collecting gel which precedes the separation gel. The collecting gel allows the proteins to be collected and compressed in the zone bordering the separation gel to form sharper zones of the individual protein bands.

Figure 5A:
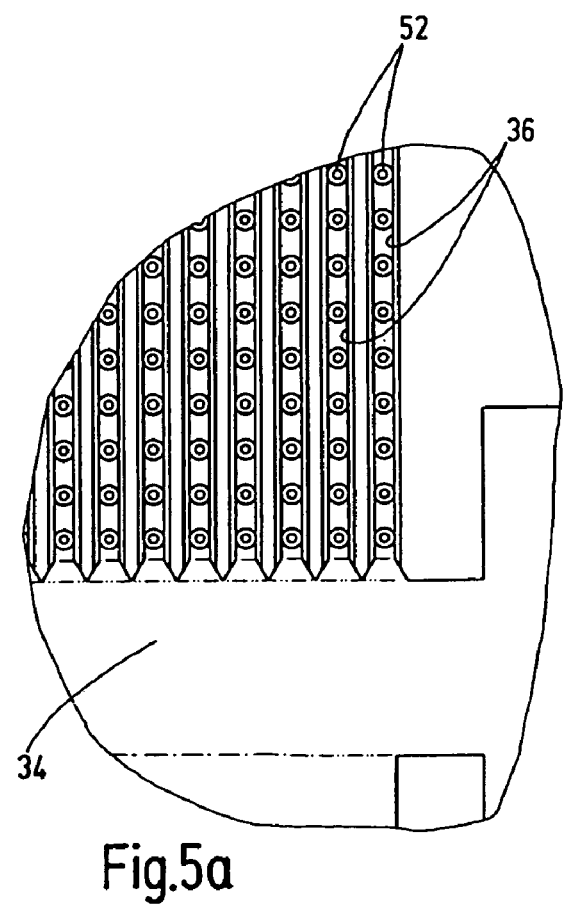
FIG. 5a shows a top-view of a section of the separation plate according to FIG. 4 and of the channel structure that adjoins the bottom side thereof.
Figure 5B:
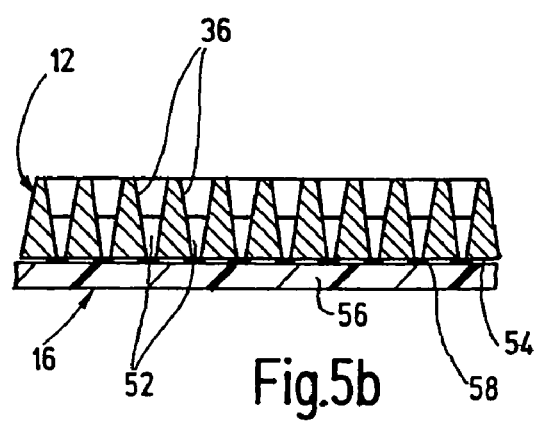
FIG. 5b shows a section of FIG. 5a with a support plate attached to the channel structure.

As shown best in FIGS. 5*a, b*, the channel structure is formed by discharge channels 52 lined up at the bottom of the separation channels 36. These extend perpendicular to the separation plane spanning the separation channels 36 and form a channel matrix spread over the separation area to enable the 2D pattern obtained in the molecular separation to be discharged as a faithful image as is elucidated in more detail below. The number of discharge channels 52 per separation channel 36 depends in turn on the desired and achievable resolution of the separation in the second dimension. It can be between 10 and 1000 and preferably 30 to 400. The discharge channels 52 are preferably conically tapered and, for example, have an upper inlet diameter of 100 μm and a lower opening cross-section of 50 μm (FIG. 5*b*). However, other channel geometries are also conceivable in order, after the separation is completed, to process the proteins in the third dimension with as little loss as possible.

For this purpose, the bottom plate 20 (FIG. 3) can be removed and the separation plate placed with its lower side 54 on a support plate 56 provided for mass spectroscopic analyses and in particular a target plate designed for matrix-assisted laser desorption/ionization time-of-flight mass spectrometry (MALDI-TOF). The support plate can consist of various materials (metals, plastics, polymers). It is important that the material is compatible with the subsequent mass spectrometry and is in particular conductive for MALDI-TOF. Hydrophilic anchor zones 58 for the substances to be transferred can be arranged on a hydrophobic surface of the support plate 56 in accordance with the two-dimensional distribution of the discharge channels 52. The position and size of these anchor zones are adapted to the discharge channels such that the eluted molecule fragments can be directly captured, and the geometric resolution that is reached in the separation process is essentially retained on the target plate.

Figure 5C:
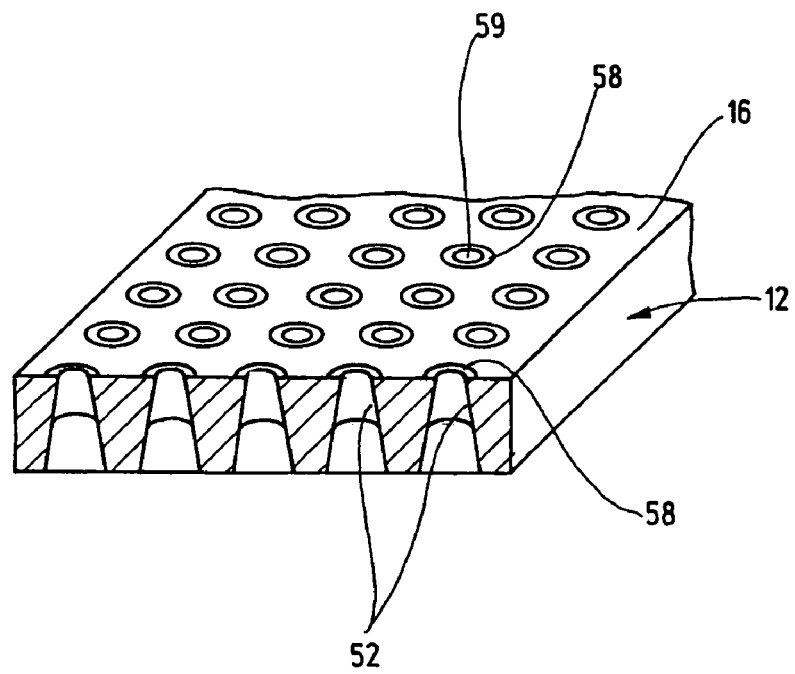
FIG. 5c shows an embodiment with a support surface directly on the separation plate in a partially cut-out perspective view.

In the particularly simple embodiment shown in FIG. 5*c*, the support surface 16 is formed by a free surface of the separation plate 12 itself. It is advantageous when the support surface 16 has circular hydrophilic anchor zones 58 for the sample material around the outlets 59 of the discharge channels 52 but is otherwise hydrophobic. This can be achieved by appropriate chemical derivatization or coating. Well-shaped depressions around the outlet openings of the discharge channels 52 can also ensure an improved deposition of the discharged peptides on the surface 16 (not shown). Also in this case, the geometric resolution achieved in the separation process should be retained. The separation plate 12 with the peptides deposited on its surface 16 is then inserted into a suitable holder for mass spectroscopy and subjected to a mass spectroscopic analysis. In this process, the peptides are directly desorbed from the surface 16 of the separation element by means of a laser.

The channels 34, 36, 52 of the three dimensions can be in continuous direct contact or be separated by barriers or valves which are only opened during transfer from one dimension into another. The contact can be mechanical or be made by moving or rotating the channels, or mechanical barriers may be provided. The channels can also be separated chemically, e.g., by polymers that are dissolved at the desired time. It is also conceivable to separate the channels of the various dimensions by semi-permeable membranes whose permeability can be regulated.

Figure 6:
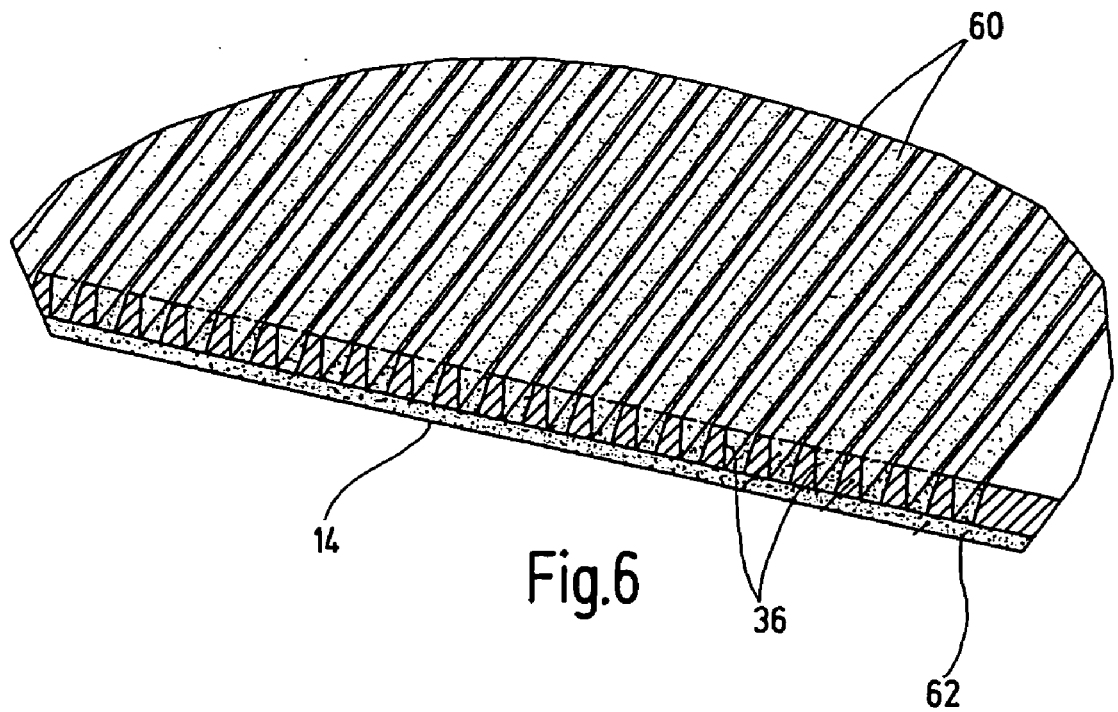
FIGS. 6 and 7 show further embodiments of separation elements in a sectional perspective view.

In the embodiment shown in FIG. 6, the separation channels 36 of the second dimension filled with SDS-PAGE separation gel 60 are bounded at the bottom by a porous bottom layer or frit 62 which, by means of micropores that fluidically communicate with one another, forms a flow-through channel structure at right angles to the separation plane. In this sense, the many pores of the bottom layer 62 that lie very close to one another are to be understood as microscopic discharge channels.

Figure 7:
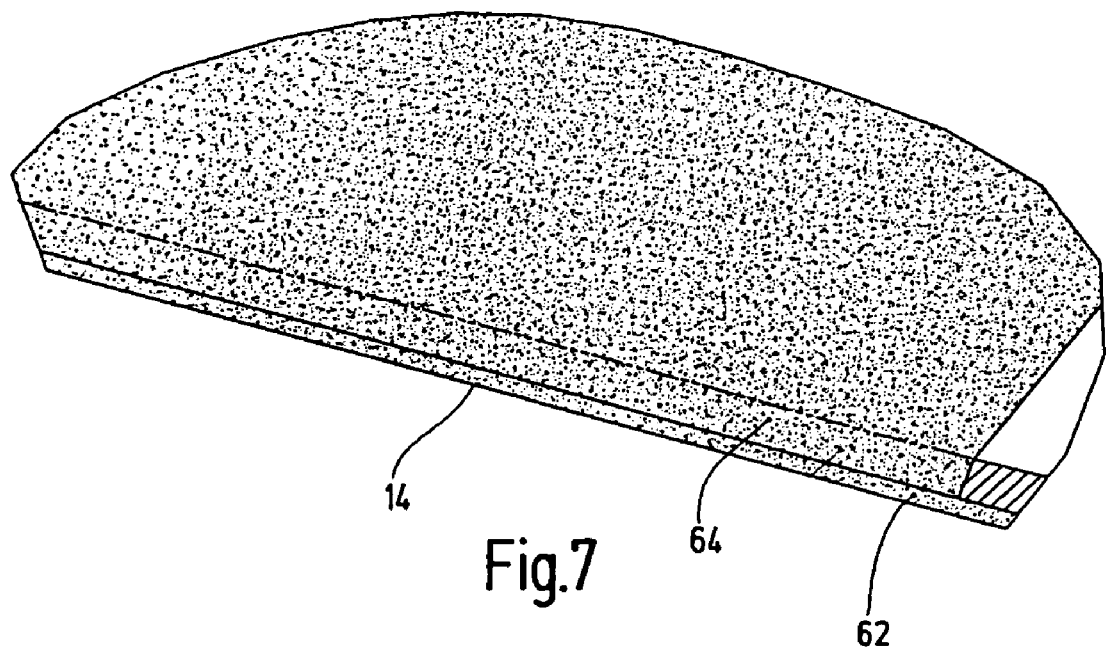

The embodiment example shown in FIG. 7 additionally differs in that instead of discrete separation channels for the separation in the second dimension, an ultrathin polyacrylamide gel layer 64 is provided which optionally laterally adjoins the IEF gel strips optionally via an intermediate strip consisting of a collecting gel and enables an SDS-PAGE electrophoresis.

Figure 8:
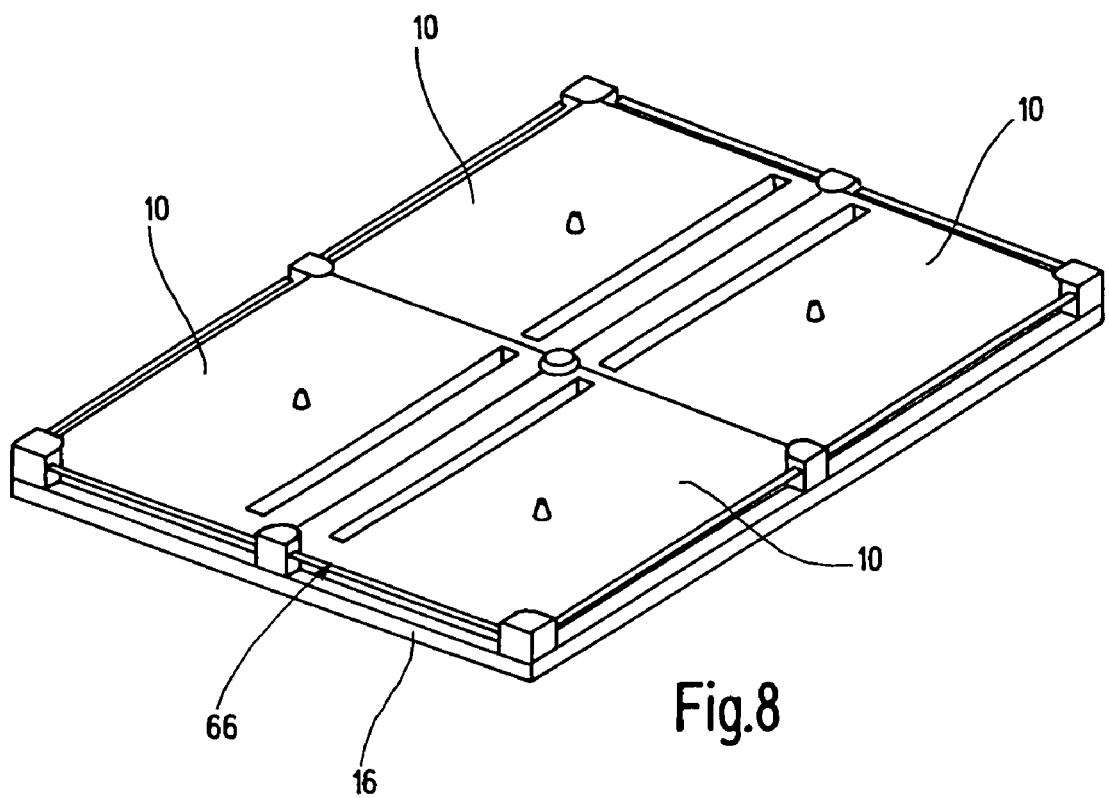
FIG. 8 shows a positioning frame to connect several separation elements to a mass spectroscopic support plate in a graphical representation.

As shown in FIG. 8, four separation elements 10 can be positioned and processed together in a positioning frame 66 on a mass spectroscopic support plate 56 having the dimensions of a microtitre plate. In this case the support plate 56 is positioned at a predetermined distance parallel to the outlet side of the respective channel structure 14 such that the molecules to be transferred can be directly transferred onto the hydrophilic anchor zones 58.

Figure 9:
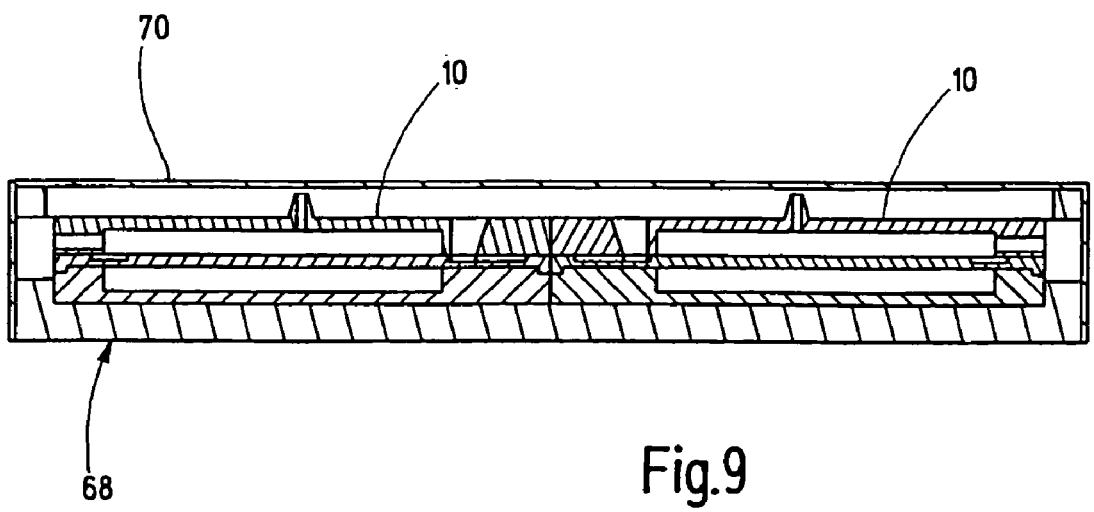
FIG. 9 shows a holding unit for storing and processing separation elements in a vertical section.

This arrangement accordingly allows the separation elements 10 to be inserted into a storage container 68 for storage and preprocessing and be enclosed therein in an air-tight manner by means of a detachable cover foil 70 (FIG. 9). The transfer into the positioning frame 66 while removing the bottom plates 20 can be simplified or automated by a suitable slide mechanism (not shown). The entire separation device comprises other units for controlling the process sequence which are known to a person skilled in the art and do not have to be individually elucidated here.

A suitable amount of the sample material is introduced into the first separation path 34 via the application opening 22 for processing in the separation element or chip 10. One μg total protein in a volume of ca. 50 nl to 1 μl carrier fluid is added for a typical separation. In the presence of a suitable buffer and after applying an electrical voltage to the electrodes 38, the proteins migrate in the electrical field and pH gradient to a position corresponding to their isoelectric point. After the separation is completed in the first dimension, which is time controlled and completed after about 1 hour, the isoelectric focusing is ended by switching off the electrical voltage.

Basically other separation methods are also possible, e.g., based on the hydrophobicity of the proteins (hydrophobic interaction) or based on their affinity to certain substances (affinity separation). The ability to carry out various separation methods in the first dimension in addition to isoelectric focusing enables protein classes to be analysed which have previously not been amenable to analysis or only to a very inadequate extent. Thus hydrophobic interaction enables membrane proteins to be analysed while affinity separation or ionic interactions enables other classes, e.g., DNA-binding proteins, to be separated. In chromatographic methods, the proteins migrate in a flow of liquid and are retarded to different extents due to their interaction with the chromatographic material. A stable equilibrium state is not formed during this interaction, but rather the separation is dynamic and has to be stopped after a certain time.

For the separation in the second dimension, it may be necessary to remove the buffer which was used for the separation in the first dimension from the proteins and to re-equilibrate them in a buffer suitable for separation in the second dimension. This can take place directly in channel 42 by overlayering, in which case the new buffer is added via the cover plate 18. The SDS-PAGE buffer is also then filled into the two buffer reservoirs 46, 48. Subsequently a voltage is applied to the two electrodes 40, and the IEF-focused proteins migrate from the IEF strips corresponding to the position they have reached into a corresponding channel 36 of the second dimension. The separation of the proteins in the SDS-polyacrylamide-filled channels 36 of the second dimension then takes place electrophoretically, during which the various proteins are separated according to their molecular weight. This SDS-PAGE gel electrophoresis, which can be monitored by adding suitable marker substances, is completed after about one hour. The electrical voltage is then switched off. Alternatively it is also of course possible to use the separation methods of the first dimension that have already been described above (IEF, hydrophobic interaction, affinity, ionic interaction) for the separation in the second dimension.

The further processing of the proteins up to their discharge from the support surface 16 takes place in a liquid flow across the channel structure 14. The required liquids are passed in via the cover chamber 24 while the valve opening 28 allows displaced air to be vented. The liquid flow is passed through the separation area 30 perpendicular to the separation plane and in a uniform distribution during which the propelling pressure difference can for example be increased by applying a supporting vacuum to the collecting chamber 32 of the bottom plate 20. The homogeneous two-dimensional distribution can be optionally improved by a perforated plate (not shown) which covers the channels 36.

In a first processing step for the subsequent mass spectroscopic analysis, SDS-free buffer solution is directed through the gel into the channels 36 of the second dimension. This removes SDS from the gel and from the separated proteins without changing the position of the proteins. The buffer solution is discharged through the channel structure 14 into the lower collecting chamber 32 of the bottom plate 20. Subsequently an exactly dosed amount of trypsin solution is added in the same manner. The trypsin cleaves the proteins into defined polypeptides. In this process the concentration and flow of trypsin is controlled in such a manner that the proteins are cleaved as completely as possible without already eluting significant amounts of the cleavage products from the gel.

After this step, the bottom plate 20 with the waste eluates is removed by a slide mechanism. Then the protein fragments generated by the protease cleavage are eluted through the discharge channels 52 by adding a defined volume of elution buffer through the cover plate and targeted flow through the separation gel. The volume is controlled such that the peptides generated from the separated proteins by protease cleavage are deposited as completely as possible through the channel structure onto the support surface 16 and are localized in the area of the outlet openings 59 of the discharge channels 52.

As a result, a transfer image of the molecular distribution in the separation area is formed on the support surface 16. Hence the separation of the proteins and the preparatory processing for mass spectrometry can be integrated in a chip using minimal amounts of materials without requiring an external intervention with transfer instruments such as micropipettes.

What is claimed is:

1. A separation device for protein mixtures comprising a separation element for two-dimensional separation of components of sample material in the area of a separation plane, wherein the separation element has a flow-through channel structure for transporting and discharging separated sample components onto a support surface in a transport direction that runs transverse to the separation plane, wherein the channel structure extends over the separation area of the separation element such that the positions relative to one another of the separated sample components are essentially retained when they are discharged onto the support surface.

2. The device of claim 1, wherein the support surface is formed by a free surface of the separation element or by a separate support substrate.

3. The device of claim 2, wherein a free transfer surface of the channel structure can be coupled to the support substrate.

4. The device of claim 2, wherein the support substrate is formed by a support plate designed for mass spectroscopic analyses and in particular by a MALDI-TOF target plate.

5. The device of claim 1, wherein the channel structure has a plurality of discharge channels that are distributed in a grid-like or matrix-like manner over the separation area of the separation element and are perpendicular to the separation plane.

6. The device of claim 1, wherein the channel structure is formed by a porous plate or layer and the pores form microscopic flow-through discharge channels perpendicular to the separation plane.

7. The device of claim 1, wherein the support surface is designed to be compatible with mass spectroscopic analyses and in particular MALDI-TOF analysis.

8. The device of claim 1, wherein the support surface has hydrophilic anchor zones for the sample material in the outlet area of the discharge channels.

9. The device of claim 1, wherein the separation element has orthogonal separation paths running in the separation plane for two-dimensional sample separation.

10. The device of claim 9, wherein the separation paths are designed for electrophoretic molecule separation in particular by isoelectric focusing (IEF) or polyacrylamide gel electrophoresis (PAGE).

11. The device of claim 9, wherein a group of adjacent separation paths of the second dimension branch off laterally at a separation path of the first dimension.

12. The device of claim 9, wherein the separation paths of at least the second dimension allow a flow at right angles in order to elute sample material.

13. The device of claim 9, wherein the separation paths are formed in particular by capillary-like microscopic separation channels and/or by separation layers of polymer or of gel material for example of polyacrylamide gel.

14. The device of claim 9, wherein the separation paths of the first and second dimension can be selectively separated from one another and/or from the channel structure by barriers or valves.

15. The device of claim 1, wherein the separation element has a perforated plate aligned parallel to the separation plane to allow passage of a liquid flow distributed over the surface.

16. The device of claim 1, further comprising a positioning frame to fix one or more separation elements relative to the support surface at defined relative positions.

17. A method for separating proteins in a sample comprising separating the proteins into a two-dimensional distribution in a separation plane of a separation element and discharging the separated proteins at right angles to the separation plane onto a support surface through a plurality of discharge channels distributed over the separation plane and at right angles thereto.

18. The method of claim 17, wherein the separated proteins are discharged in a matrix-like or grid-like manner onto the support surface in a manner corresponding to the two-dimensional distribution in the separation plane.

19. The method of claim 17, wherein the proteins are prepared for a mass spectroscopic analysis directly in the separation element after the two-dimensional separation.

20. The method of claim 17, wherein the separated proteins are processed in a liquid flow aligned at right angles to the separation plane, the processing comprising washing, cleaving, and discharging.

21. The method of claim 17, wherein the separated proteins are discharged onto a surface of the separation element and are then directly analyzed on this surface by MALDI-TOF analysis.

22. The method of claim 17, wherein the separated proteins are transferred from the separation element onto a MALDI-TOF plate forming the support surface.

* * * * *

UNITED STATES PATENT AND TRADEMARK OFFICE
CERTIFICATE OF CORRECTION

PATENT NO. : 7,645,369 B2 Page 1 of 1
APPLICATION NO. : 11/120098
DATED : January 12, 2010
INVENTOR(S) : Hoeltke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1259 days.

Signed and Sealed this

Sixteenth Day of November, 2010

David J. Kappos
*Director of the United States Patent and Trademark Office*